(12) United States Patent
Dandala et al.

(10) Patent No.: US 7,164,022 B2
(45) Date of Patent: Jan. 16, 2007

(54) PROCESS FOR THE PREPARATION OF PURE FINASTERIDE

(75) Inventors: Ramesh Dandala, Hyderabad (IN); Divvela Venkata Naga Srinvasa Rao, Hyderabad (IN); Koilpillai Joseph Prabahar, Tirunelveli (IN); Gollapalli Venkateswara Rao, Hyderabad (IN); Meenakshisunderam Sivakumaran, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 11/252,860

(22) Filed: Oct. 18, 2005

(65) Prior Publication Data
US 2006/0084671 A1 Apr. 20, 2006

(30) Foreign Application Priority Data
Oct. 18, 2004 (IN) .................. 1086/CHE/2004

(51) Int. Cl.
*C07D 221/18* (2006.01)
*C07D 221/04* (2006.01)
(52) U.S. Cl. .......................... 546/77; 546/61
(58) Field of Classification Search .......... 546/77, 546/61
See application file for complete search history.

(56) References Cited
U.S. PATENT DOCUMENTS
5,084,574 A * 1/1992 Bhattacharya et al. ........ 546/77

* cited by examiner

*Primary Examiner*—Charanjit S. Aulakh
(74) *Attorney, Agent, or Firm*—Jay R. Akhave

(57) ABSTRACT

The present invention relates to an improved process for the preparation of pure Finasteride of Formula I, Formula I which comprises converting dihydrofinasteride to finasteride through novel protected dihydrofinasteride and protected finasteride intermediates.

12 Claims, No Drawings

PROCESS FOR THE PREPARATION OF PURE FINASTERIDE

CROSS REFERENCE TO THE RELATED APPLICATION

This application claims the priority of provisional application No: 1086/CHE/2004, filed on Oct. 18, 2004 in India.

FIELD OF THE INVENTION

The present invention relates to an improved process for the preparation of pure Finasteride of Formula I,

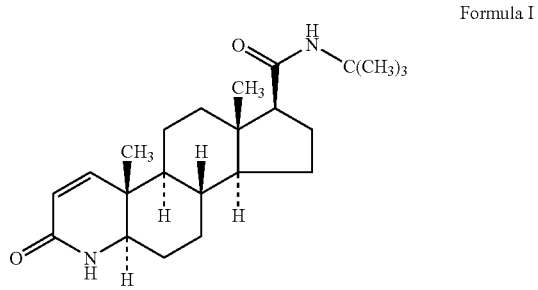

Formula I

BACKGROUND OF THE INVENTION

Finasteride, also known as N-(5α,17β)-N-(1,1-dimethylethyl)-3-oxo-4-azaandrost-1-ene-17-carboxamide, is a 5α-reductase inhibitor, functions in many androgen-sensitive tissues by converting the major circulating androgenic hormone, testosterone, into the intracellular androgenic metabolite dihydrotestosterone (DHT). Finasteride is used in the treatment of hyperandrogenic conditions, such as acne vulgaris, seborrhea, female hirsutism and benign prostate hypertrophy.

Finasteride was first disclosed in U.S. Pat. No. 4,760,071, which describes a process wherein the carboxylic group at the 17β-position of 3-oxo-4-aza-5a-androstane-17β-carboxylic acid of formula (II) is converted into a pyridylthioester group of formula (III) using 2,2'-pyridyldisulfide. The compound of formula (III) is reacted with tert-butylamine to obtain 17β-tert-butylamide of formula (IV), followed by introducing a double bond between the first and the second carbon atoms using benzeneselenic anhydride in boiling chlorobenzene to obtain finasteride of formula (I). However, this process suffers from a high production cost due to the usage of expensive reagents such as 2,2'-pyridyldisulfide and bezeneselenic anhydride, and a poor purity, due to the formation of undesired by-products. Further, it is difficult to improve the purity of the obtained finasteride even after purification steps such as column chromatography and recrystallization.

Scheme -1

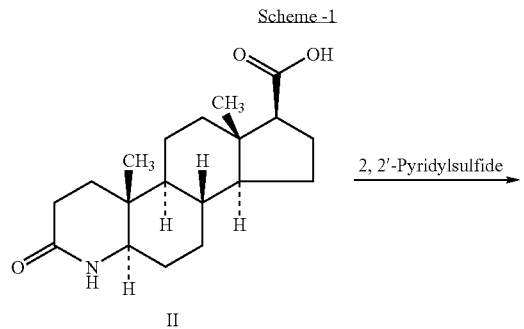

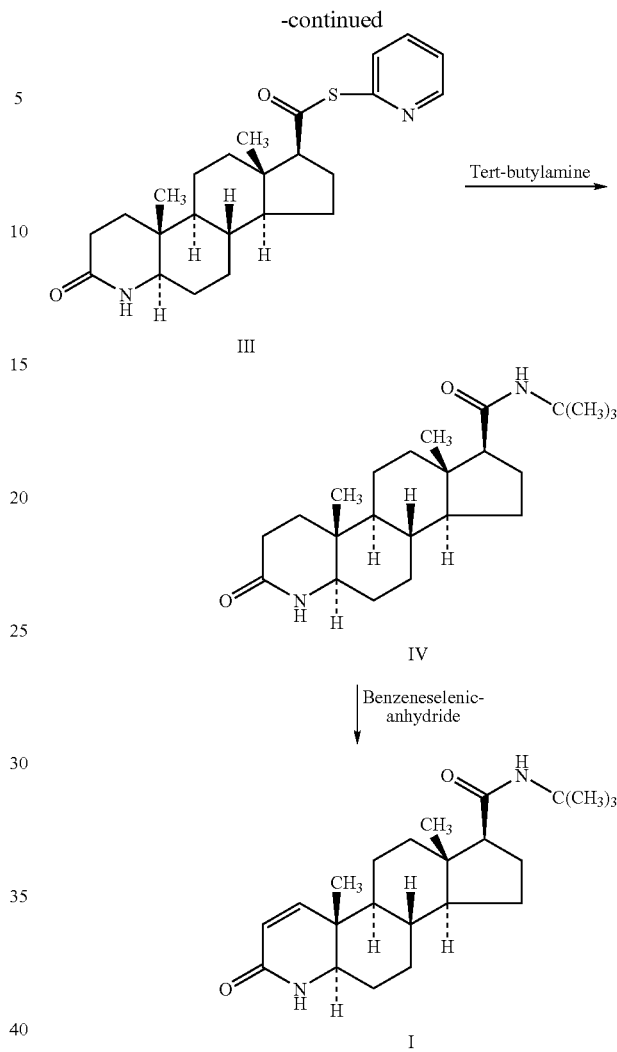

U.S. Pat. No. 5,084,574 discloses a process for preparing finasteride, which comprises silylating the 3-oxo group in the above compound of formula (II) using bistrimethylsilyltrifluoroacetamide (BSTFA), followed by introducing a double bond using 2,3-dichloro-5,6-dicyano-1,4-benzoquinone (DDQ) as an oxidizing agent. However, the isolation of finasteride from the reaction mixture by this process is very difficult, and one obtains only impure finasteride. Further purification of finasteride at this stage is much more difficult, therefore, it is not suitable for mass production.

U.S. Pat. No. 5,091,534 describes a process for preparing finasteride, which comprises silylating the compound of the formula (II) in the presence of a base and introducing a halogen such as iodine and bromine into the 2-position of the compound, followed by introducing a double bond between the first and the second carbon atoms using a strong base such as potassium tert-butoxide, 1,8-diazabicyclo [5.4.0] undec-7-ene (DBU) and 1,5-diazabicyclo [4.3.0] non-5-ene (DBN).

However, this process also suffers from product of a poor quality, since the reactants and products tend to decompose due to the high pH of the reaction solution owing to the strong base.

U.S. Pat. No. 5,021,575 describes a process wherein azasteroid has been first treated with oxalyl chloride to protect amide nitrogen and oxygen and then subjected to bromination to prepare 2-bromo derivative of azasteroid. Thereafter 2-bromo derivative is deprotected first, followed by dehydrohalogenation to create Δ1,2-double bond. However, this process involves complicated reactions leading to unwanted by-products.

U.S. Pat. No. 6,762,302 describes the bioconversion process to effect dehydrogenation during preparation of finasteride. However, the best reported yield was 80% conversion and furthermore this patent does not teach, how to remove the unreacted dihydrofinasteride, which is difficult to remove by crystallization.

As discussed, the above described methods for preparing finasteride are disadvantageous in that they employ expensive and toxic reagents, require extreme reaction conditions or comprise complicated multiple steps, thereby rendering them unsuitable for mass production. Accordingly, there has been a need to develop a simple and industrially viable process by using novel intermediates of formula V and formula VI (protected finasteride), which can be easily purified to obtain a highly pure finasteride, in higher yield.

OBJECTIVE OF THE INVENTION

The main objective of the invention is to provide an improved process for the preparation of Finasteride with high purity and yield.

SUMMARY OF THE INVENTION

The present invention relates to an improved process for the preparation of Finasteride of Formula I,

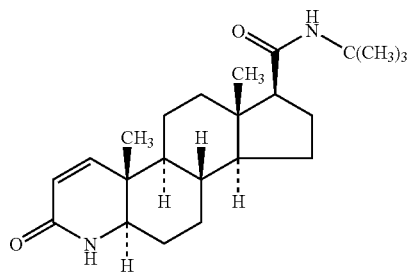

Formula I which comprises, protecting dihydrofinasteride of formula IV,

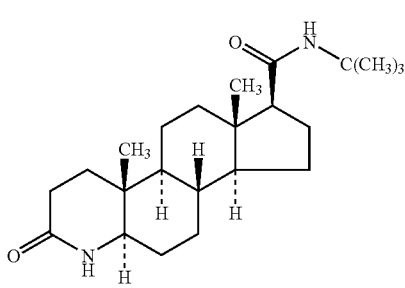

Formula IV with suitable protecting group in an organic solvent to obtain a compound of formula V,

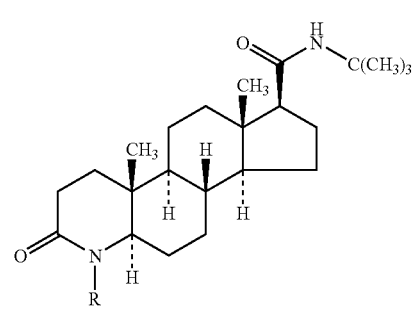

Formula V wherein R is protecting group;

treatment of protected dihydrofinasteride of formula (V), with a silylating agent followed by quinone with or without acid catalyst to obtain protected finasteride of formula VI,

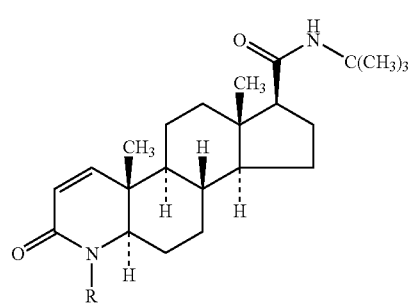

Formula VI wherein R is protecting group, deprotection of compound of formula VI in acidic or basic condition to obtain Finasteride of formula I.

DETAILED DESCRIPTION OF THE INVENTION

The present invention relates to an improved process for the preparation of Finasteride with high purity and in high yield.

According to one embodiment of the present invention, protected dihydrofinasteride of formula V is prepared by the protection of the amide nitrogen of dihydrofinasteride of formula IV, with suitable protecting group in an organic solvent. The protecting group may be selected from the group benzoyl, substituted benzoyl, benzyl, substituted benzyl, benzhydryl, and the like. The reaction is carried out using organic solvents. The organic solvent is selected from hydrocarbons such as hexanes, toluene, benzene and xylenes; halogenated hydrocarbons such as methylene chloride, ethylenedichloride or carbon tetrachloride; ketones such as acetone or methyl ethyl ketone; esters such as ethyl acetate or isopropyl acetate; and the like or mixtures thereof. The protecting agent may be employed in an amount ranging from 0.9 to 2.0 mole equivalents, preferably 0.9 to 1.0 per mole of compound (IV). The reaction conditions depend on the protecting group and protection is effected using methods known in the prior art.

In another embodiment of the present invention protected dihydrofinasteride of formula V, is subjected to dehydrogenation reaction to obtain a compound of formula VI. The reaction involves the treatment of protected dihydrofinasteride with a silylating agent in the presence of a quinone derivative.

The silylating agent is selected from bistrimethylsilylacetamide, bistrimethylsilyltrihaloacetamide, hexamethyldisilazane or bistrimethylsilylurea. The bistrimethylsilyltrihaloacetamide silyating agent can have any halo group as a moiety thereof, such as chloro, fluoro, bromo or iodo. The preferred silylating agent is bistrimethylsilyltrifluoroacetamide (BSTFA).

The quinone derivative is selected from 3,4-dichloro-5, 6-dicyano-1,4-benzoquinone (DDQ), 3,4,5,6-tetrachloro-1, 2-benzoquinone, ortho- or para-benzoquinones and the like and preferably 3,4-dichloro-5,6-dicyano-1,4-benzoquinone (DDQ) is used.

The organic solvent which is used in the present invention includes aliphatic or cyclic ethers selected from, diethylether, diisopropylether or dimethoxyethane, dioxane or tetrahydrofuran or chlorinated solvents selected from methylenechloride, ethylenedichloride or carbon tetrachloride or aromatic hydrocarbon solvents selected from toluene, benzene, xylenes etc; with or without acid catalysts selected from triflic acid, m-chlorobenzoic acid, peracetic acid, trifluoroperacetic acid, preferably triflic acid. Thereafter, the deprotection of protected finasteride of formula (VI) is carried out using acidic or basic conditions, preferably carried out under basic conditions using hydrazines, alkyl amines selected from methyl amine, ethylamine, di-isopropyl amine.

The major advantages realized in the present invention includes, the protected Finasteride of formula VI is obtained in a highly pure form, which on further deprotection results in pure Finasteride in high yield and low cost. With the process of the present invention dihydrofinasteride of formula IV, which is an impurity in the finasteride can be removed to less than 0.1%, whereas when the finasteride is prepared with the prior-art processes this impurity cannot be removed when present in higher quantities.

The present invention also relates to novel compounds of formula V and formula VI, which are used in the preparation of finasteride.

The details of the process of the invention are provided in the examples given below, which are provided by way of illustration only and therefore should not be construed to limit the scope of the invention.

EXAMPLE

Step A: Preparation of Benzoyl Dihydrofinasteride

4-Dimethylamino pyridine (21.3 g, 0.17 mol) was added to a suspension of dihydrofinasteride (50 g, 0.23 mol) in toluene (500 ml). To this reaction mass benzoyl chloride (24.5 g, 0.17 mol) was added slowly at a temperature below 40° C., and thereafter heated at reflux for 4 hrs. Reaction mass was concentrated under reduced pressure. The residue was dissolved in methylene chloride (300 ml) and washed with DM water (2×150 ml). The methylene chloride layer was concentrated to dryness and the product was precipitated with methanol (150 ml), filtered and dried to get the title compound.

Step B: Preparation of Benzoyl Finasteride

Benzoyl dihydofinasteride (50 g, 0.10 mol), DDQ (28.6 g, 0.125 mol), triflic acid (1.25 g, 0.008 mol) and bis (trimethylsilyl) trifluoro acetamide (BSTFA, 95 gm, 0.37 mol) were added to xylene (500 ml) and maintained at room temperature for 1 hr. Thereafter, the reaction mass was heated at reflux for 4 hrs, cooled and washed with 10% aqueous sodium metabisulfite solution followed by DM water at 65–70° C. The organic layer was concentrated under reduced pressure. The product was precipitated by adding methanol (150 ml), filtered and dried to obtain the finasteride.

Step C: Preparation of Finasteride

Benzoyl finasteride (15 gm, 0.31 mol) and 70% aqueous ethyl amine solution (10.13 g, 0.16 mol)) were added to ethanol (90 ml) and heated at reflux for 2 hrs. Concentrated the reaction mass under reduced pressure, diluted with water (100 ml) and further acidified with acid. The product was precipitated from THF and ethyl acetate mixture, filtered and dried to obtain Finasteride.

We claim:

1. A before process for the preparation of Finasteride of Formula I,

Formula I

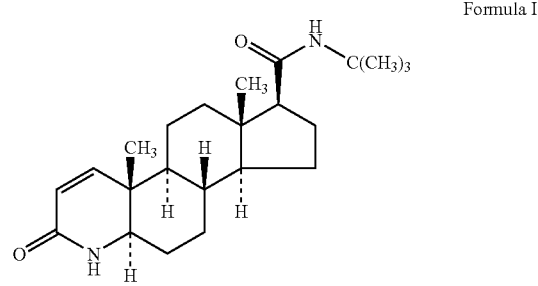

which comprises,
protecting dihydrofinasteride of formula IV,

Formula IV with suitable protecting group selected from benzoyl, substituted benzoyl, benzyl, substituted benzyl or benzhydryl group in an organic solvent to obtain a compound of formula V, Formula V wherein R is a protecting group;
treatment of protected dihydrofinasteride of formula V with a silylating agent followed by quinone derivative with or without acid catalyst to obtain protected finasteride of formula VI,

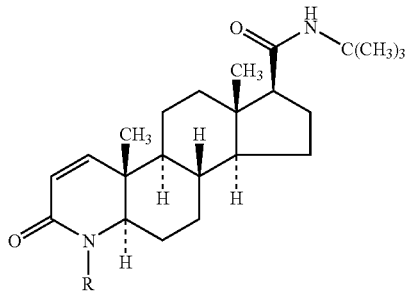

Formula VI wherein R is a protecting group,
deprotection of compound of formula VI in an acidic or basic conditions to obtain Finasteride of formula I.

2. A process according to claim 1, wherein the said protecting group is a substituted benzoyl, or benzoyl group.

3. A process according to claim 1, wherein the said organic solvent is selected from the group consisting of hydrocarbons, halogenated hydrocarbons, ketones, esters, and mixtures thereof.

4. A process according to claim 1, wherein the said silylating agent is bistrimethylsilylacetamide, bistrimethylyltrihaloacetamide, hexamethyldisilazane or bistrimethylsilylurea.

5. A process according to claim 4, wherein the halo group in bistrimethylsilyltrihaloacetamide silyating agent is a chloro, fluoro, bromo or iodo group.

6. A process according to claim 5, wherein the preferred silylating agent is bistrimethylsilyltrifluoroacetamide (BSTFA).

7. A process according to claim 1, wherein the said quinone derivative is selected from the group consisting of 3,4-dichloro-5,6-dicyano-1,4-benzoquinone (DDQ), 3,4,5,6-tetrachloro-1,2-benzquinone, ortho-benzoquinone and para-benzoquinone.

8. A process according to claim 1, wherein the said acid catalyst is selected from group consisting of triflic acid, m-chlorobenzoic acid, peracetic acid and trifluoroperacetic acid.

9. A process according to claim 1, wherein the deprotection step is carried out preferably under basic conditions using hydrazine or alkyl amines.

10. A process according to claim 9 wherein the said alkyl amine is methylamine, ethylamine or di-isopropylamine.

11. The compound of formula V,

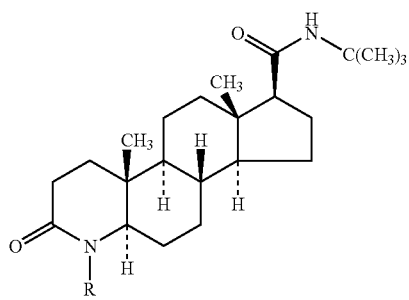

Formula V wherein the protecting group R is a substituted benzoyl, benzoyl, benzyl, substituted benzyl or benzhydryl group.

12. The compound of formula VI,

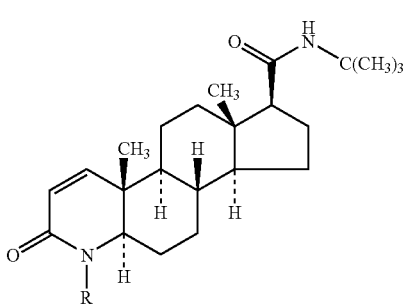

Formula VI wherein the protecting group R is a substituted benzoyl, benzoyl, benzyl, substituted benzyl or benzhydryl group.

* * * * *